United States Patent [19]

Padovan et al.

[11] 4,146,732

[45] Mar. 27, 1979

[54] PROCESS FOR PREPARING UNSATURATED CARBOXYLIC ACIDS BY THE CATALYTIC OXIDATION IN THE GAS PHASE OF THE CORRESPONDING ALDEHYDES

[75] Inventors: Mario Padovan, Milan; Giancarlo Battiston, Baranzate; Francesco Pignataro, Gallarate; Giordano DeAlberti, Besnate; Giuseppe Leofanti, Arese, all of Italy

[73] Assignee: Montedison S.p.A., Milan, Italy

[21] Appl. No.: 797,671

[22] Filed: May 17, 1977

[30] Foreign Application Priority Data

May 20, 1976 [IT] Italy ................. 23448 A/76

[51] Int. Cl.$^2$ ................. C07C 51/32; C07C 57/04
[52] U.S. Cl. ................. 562/534; 252/470
[58] Field of Search ................. 260/530 N; 252/470

[56] References Cited

U.S. PATENT DOCUMENTS

| | | | |
|---|---|---|---|
| 3,322,693 | 5/1967 | Bethell et al. | 260/530 N |
| 3,736,354 | 5/1973 | Yanagita et al. | 260/530 N |
| 4,014,925 | 3/1977 | Feralazzo et al. | 260/530 N |

*Primary Examiner*—Vivian Garner
*Attorney, Agent, or Firm*—Stevens, Davis, Miller & Mosher

[57] ABSTRACT

A process is disclosed for preparing unsaturated carboxylic acids consisting essentially in reacting in the vapor phase an unsaturated aldehyde with molecular oxygen or an oxygen-containing gas, at a temperature ranging from 200° to 370° C., in the presence of a solid catalyst, with a contact time between 0.5 and 5 seconds, characterized in that the catalyst consists essentially of molybdenum, vanadium, cobalt, and optionally tungsten, these elements being chemically combined with oxygen and the atomic ratios of the elements being represented by the empirical formula $Mo_{12}V_aW_bCo_cO_d$ a is between 1.5 and 3.0;
b is between 0 and 0.5;
c is between 3.5 and 5.5; and
d is a number sufficient to satisfy the valences of the other elements, said catalyst being prepared starting from aqueous solutions of soluble salts of the elements composing it, by the coprecipitation method. Preferably, the coprecipitation is effected at a pH ranging from 2 to 5 and at a temperature between 20° and 90° C., by adding to a first solution containing cobalt in the form of the nitrate, a second solution containing molybdenum, vanadium, and optionally also tungsten, in the form of ammonium salts. The catalyst may be deposited on a carrier. Acrolein may be oxidized to acrylic acid, or methacrolein oxidized to methacrylic acid.

6 Claims, No Drawings

PROCESS FOR PREPARING UNSATURATED CARBOXYLIC ACIDS BY THE CATALYTIC OXIDATION IN THE GAS PHASE OF THE CORRESPONDING ALDEHYDES

The present invention relates to a process for preparing unsaturated carboxylic acids by the catalytic oxidation in the vapor phase with molecular oxygen, or with an oxygen-containing gas, of low molecular weight unsaturated aldehydes containing more than two carbon atoms. The invention is particularly useful for producing acrylic acid from acrolein, or methacrylic acid from methacrolein.

The process according to this invention is characterized in that the unsaturated aldehyde is oxidized in the presence of a catalyst composed of or consisting essentially of molybdenum, vanadium, cobalt and, optionally, tungsten, these elements being chemically combined with oxygen.

The relative atomic ratios of the elements in the catalyst according to the present invention correspond to the following empirical formula:

$$Mo_{12} V_a W_b Co_c O_d$$

wherein:
a is between 1.5 and 3.0, the preferred range being however 2.0 to 2.4;
b is between 0 and 0.5, the preferred range being however 0 to 0.3;
c is between 3.5 and 5.5, the preferred range being however 3.9 to 4.3; and
d is a number sufficient to satisfy the valences of the other elements.

This empirical formula is merely intended to indicate the atomic ratios in which the various elements are present in the catalytic composition independently of and without reference to the actual chemical bonds existing among said elements.

The oxidation of the unsaturated aldehydes to the corresponding acids on catalysts composed of Mo, V, W, Co and O is already broadly known in the prior art. In particular, from U.S. Pat. No. 3,736,354, a catalyst system is known that consists essentially of Mo, V and O to which one or more elements selected from the group consisting of W and Co are added. All these catalysts are prepared by drying the solutions containing the salts of the catalytically active elements along with a silica sol, or by impregnating a preformed carrier with the solutions.

However, it has now surprisingly been found (according to the present invention) that a catalyst containing Mo, V, Co, and optionally W, when prepared according to the coprecipitation method, brings about an unexpected improvement in catalytic performance. The extent of this improvement appears clearly from a comparison between the results of Examples 1 and 5 and those of comparative Examples 1a and 5a.

Furthermore, it has been found that the catalyst prepared according to the coprecipitation method is generally characterized by a fixed stoichiometry defined, in the above-reported empirical formula, by the atomic indexes or ratios defining the preferred ranges.

The precipitation conditions, and in particular the concentration of the salts containing the active elements and their ratio in the starting solutions, sparingly or only slightly influence the stoichiometric composition of the precipitate. Examples 2, 3, 5, 6 and 7 serve to prove that, even by carrying out the precipitation with starting salts ratios very different from those of the composition considered as the preferred one, the composition of the precipitate differs very little from said preferred composition, and without prejudice to the catalytic activity. This proves that there is a coprecipitation of small amounts of free oxides deriving from only a part of the salts introduced in excess.

The preparation of the catalyst as described herein is essential for the purpose of attaining optimum catalyst performances and it is carried out conforming to the coprecipitation method.

The catalyst may be employed without a carrier, or with a suitable carrier such as, for example, silica, alumina, silica-alumina, silicon carbide, pumice etc., using for the supporting step or steps the most suited techniques well known to those skilled in the preparation of catalysts.

The catalysts of this invention are prepared starting from two limpid aqueous solutions of soluble salts of the elements constituting them.

The first solution, containing cobalt preferably in the form of nitrate and subjected to intense stirring, is additioned with the second solution containing molybdenum, vanadium and optionally also tungsten, preferably in the form of ammonium salts.

Since the catalytically active mass precipitates in a manner independently of the concentration of the salts containing the elements that constitute said mass and independently of their ratios in the starting solutions, it is not necessary to prepare these solutions according to stoichiometric ratios. However, this is highly desirable with a view to achieving high precipitation yields, which may be in the order of 90% and even higher.

The precipitation pH value ranges from 2 to 5, while the temperature may vary from 20° to 90° C., the preferred range being from 50° to 70° C.

The time required for the precipitation is not determinant for the purpose of obtaining a good catalyst. Thus, the time may vary over a very wide range, depending also on the amount of treated salts: generally it is between 15 minutes and 3 hours.

At the conclusion of the precipitation the mass is separated from the solution, which is then washed and subjected to a number of thermal treatments in air, comprising a drying step at 90°–130° C. for a time period of 10–20 hours, a successive calcining step at a temperature of from 200° to 300° C. for a time period of 6–24 hours, and an activation step at a temperature ranging from 350° to 450° C. for a time period not shorter than 2 hours.

The process according to the present invention can be carried out in any type of reactor suited for conducting the oxidation in the gas phase. For examples one may utilize fixed bed or fluid bed reactors.

The reaction temperature is between 200° and 370° C., and the reaction may be conducted at atmospheric pressure, or under superatmospheric pressure, for example, up to 10 Kg/cm² absolute.

The contact time, defined as the ratio between the catalyst apparent volume and the volume of the gas fed under the reaction conditions, per time unit, ranges from 0.5 to 5 seconds.

The unsaturated aldehyde concentration is preferably between 2.5 and 8.5% by volume in respect of the feeding mixture. The molar ratio between the oxygen and the unsaturated aldehyde preferably ranges from 0.5 to 6. The oxygen required for the oxidation process may be fed in pure or substantially pure form, but if no particular reasons exist for using the substantially pure oxygen, then air is the preferred oxidizing agent.

The oxidation is preferably conducted in the presence of one or more diluents, such as nitrogen, carbon dioxide, water vapor, etc. Of these possible diluents, water vapor is particularly advantageous. The water vapor concentration is preferably between 20 and 50% in respect of the feeding mixture.

The following examples are given to better illustrate the invention, without being, however, a limitation thereof. The terms "conversion" and "selectivity", whenever used therein, mean respectively:

$$\text{aldehyde conversion in \%} = \frac{\text{moles of fed aldehyde} - \text{moles of unreacted aldehyde}}{\text{moles of fed aldehyde}}$$

$$\text{selectivity to product in \%} = \frac{\text{gram atoms of carbon in the product}}{\text{gram atoms or carbon in the reacted aldehyde}}$$

EXAMPLE 1

A catalyst having the composition $M_{12}V_2Co_{4.1}$ was prepared as follows:

164.9 g of $Co(NO_3)_2.6H_2O$ and deionized $H_2O$ up to a volume of 240 ml were introduced into a 2-liter flask. Dissolution was effected at room temperature under continuous stirring: the final pH of the solution was 2.2.

A solution of 282.4 g of $(NH_4)_2Mo_2O_7$ and 34.0 g of $NH_4VO_3$ in such an amount of deionized $H_2O$ that the final volume of the solution is 760 ml, was prepared separately, at a temperature of about 70° C.

In the two solutions the desired elements were present, in the aggregate, in the atomic ratios represented by the theoretical formulation $Mo_{12}V_{2.1}Co_{4.1}$.

To the former (cobalt nitrate) solution, brought to a temperature of 60° C. and kept under stirring, the latter solution was added in a time period of about 60 minutes. Stirring was then continued for a further 15 minutes. The resulting precipitate, once filtered and washed with 2 liters of cold deionized water, was dried for 12 hours at 110° C., then calcined at 250° C. for 12 hours and, finally, activated for 5 hours at 400° C., reaching the activation temperature at a heating rate of 2° C./minute.

The precipitation yield, calculated in respect of the total amount of oxides of the elements introduced in the form of salts into the starting solutions, was 90%. The solid so obtained was ground and the fraction between 60 and 80 mesh (Tyler) was collected.

7 ml of catalyst were put in the form of a fixed bed into a steel reactor having a 10 mm diameter, thermoregulated in a molten salts bath. A gaseous mixture consisting of 5.5% of acrolein, 59.5% of air, and 35% of steam was made to flow through the catalyst at a space velocity corresponding to a contact time of 1 second, and at a temperature of 280° C.

The following results were obtained:
conversion of acrolein: 97.8%
selectivity to acrylic acid: 93.3%.

EXAMPLE 1a

A catalyst having the composition $Mo_{12}V_{2.1}Co_{4.1}$ was prepared as follows:

An aqueous solution of diammonium molybdate and of ammonium metavanadate, prepared according to the procedures described in Example 1, was additioned with 13 ml of $NH_4OH$ (at 32% by weight) and put into a porcelain capsule, whereupon an aqueous solution of cobalt nitrate prepared according to Example 1 was added thereto.

Under stirring, this was evaporated to dryness on a water bath: the solid so obtained was dried at 110° C. for 12 hours, calcined at 285° C. for 12 hours, and finally activated for 5 hours at 400° C.

The reaction test, carried out according to the same procedures as described in Example 1, but at a temperature of 340° C. (which the highest acid yields correspond to), provided the following results:
conversion of acrolein: 95.2%
selectivity to acrylic acid: 59.4%.

EXAMPLE 2

A catalyst having the composition $Mo_{12}V_{2.8}Co_{3.9}$ was prepared and activated according to the procedures described in Example 1, but using 48.0 g of $NH_4VO_3$.

In the aggregate, in the two solutions the composing elements were present in the atomic ratios represented by the theoretical formulation $Mo_{12}V_{3.0}Co_{4.1}$.

The reaction test, conducted as described in Example 1, provided the following results:
conversion of acrolein: 100%
selectivity to acrylic acid: 92.5%.

EXAMPLE 3

A catalyst having the composition $Mo_{12}V_{1.6}Co_{4.6}$ was prepared and activated according to the procedures described in Example 1, but employing 16.0 g of $NH_4VO_3$.

In the aggregate, in the two solutions the composing elements were present in the atomic ratios represented by the theoretical formulation $Mo_{12}V_{1.0}Co_{4.1}$.

The reaction test conducted according to procedures described in Example 1, but at a temperature of 300° C., provided the following results:
conversion of acrolein: 99.3%
selectivity to acrylic acid: 92.7%.

EXAMPLE 4

A catalyst having the composition $Mo_{12}V_{2.1}W_{0.2}Co_{4.0}$ was prepared and activated according to the procedures described in Example 1, but adding to the ammonium salts solution also 7.1 g of $(NH_4)_6H_2W_{12}O_{40}.nH_2O$ (ammonium tungstate at 90.6% of $WO_3$) and employing the following amounts of the other salts:
168.9 g of $Co(NO_3)_2.6H_2O$
282.4 g of $(NH_4)_2Mo_2O_7$
38.9 g of $NH_4VO_3$.

In the aggregate, the composing elements were present in the two solutions in the atomic ratios represented by the theoretical formulation $Mo_{12}V_{2.4}W_{0.2}Co_{4.2}$.

The catalytic activity test carried out as described in Example 1, but at a temperature of 300° C., provided the following results:
conversion of acrolein: 100%
selectivity to acrylic acid: 95.5%.

EXAMPLE 5

A catalyst having the composition $Mo_{12}V_{2.3}W_{0.1}Co_{4.2}$ was prepared and activated as described in Example 4, but employing the following amounts of salts:
29.5 g of $Co(NO_3)_2.6H_2O$
94.1 g of $(NH_4)_2Mo_2O_7$ 10.8 g of $NH_4VO_3$ 47.2 g of ammonium tungstate containing 90.6% of $WO_3$.

The volume of the former solution (containing Co nitrate) was 450 ml, that of the latter solution was 1,000 ml.

In the aggregate, the composing elements were present in the two solutions in the atomic ratios represented by the theoretical formulation $Mo_{12}V_{2.0}W_{4.0}Co_{2.2}$.

The catalytic activity test, conducted under the same conditions as described in Example 1, yielded the following results:

conversion of acrolein: 99.4%
selectivity to acrylic acid: 94.0%.

EXAMPLE 5a

A catalyst having the composition $Mo_{12}V_{2.4}W_{0.2}Co_{4.2}$ was prepared by evaporating an aqueous solution of:

56.3 g of $Co(NO_3)_2.6H_2O$
94.12 g of $(NH_4)_2Mo_2O_7$
12.96 g of $NH_4VO_3$
2.36 g of ammonium tungstate containing 90.6% of $WO_3$.

The resulting solid, once ground for 12 hours at 110° C., calcined at 300° C. for 12 hours, and, finally, activated for 5 hours at 400° C., was ground and subjected to catalytic activity measurements according to the procedures described in Example 1, first at a temperature of 300° C. whereupon the following results were obtained:

conversion of acrolein: 93.3%
selectivity to acrylic acid: 84.9%.

At a temperature of 280° C., the following results were obtained:

conversion of acrolein: 83.9%
selectivity to acrylic acid: 87.2%.

EXAMPLE 6

A catalyst having the composition $Mo_{12}V_{2.4}W_{0.2}Co_{5.1}$ was prepared and activated according to the procedures described in Example 1, but utilizing 253.5 g of $Co(NO_3)_2.6H_2O$.

In the aggregate, the composing elements were present in the two solutions in the atomic ratios represented by the theoretical formulation $Mo_{12}V_{2.4}W_{0.2}Co_{6.3}$.

The catalytic activity test, conducted under the same conditions as described in Example 1, but at a temperature of 270° C., yielded the following results:

conversion of acrolein: 100%
selectivity to acrylic acid: 93.8%

EXAMPLE 7

A catalyst having the composition $Mo_{12}V_{2.5}W_{0.2}Co_{5.5}$ was prepared and activated according to the procedures described in Example 1, but using 337.8 g of $Co(NO_3)_2.6H_2O$.

In the aggregate, the composing elements were present in the two solutions in the atomic ratios represented by the theoretical formulation $Mo_{12}V_{2.5}W_{0.2}Co_{8.4}$.

The catalytic activity test conducted under the same conditions as in Example 1, but at a temperature of 300° C., provided the following results:

conversion of acrolein: 99.0%
selectivity to acrylic acid: 93.0%.

What is claimed is:

1. A process for preparing acrylic acid or methacrylic acid comprising reacting in the vapor phase acrolein or methacrolein, respectively, with molecular oxygen or an oxygen-containing gas, at a temperature ranging from 200° to 370° C., in the presence of a solid catalyst, with a contact time between 0.5 and 5 seconds, characterized in that the catalyst consists essentially of molybdenum, vanadium, cobalt, and optionally tungsten, these elements being chemically combined with oxygen and the atomic ratios of the elements being represented by the empirical formula $Mo_{12}V_aW_bCo_cO_d$ wherein:

a is between 1.5 and 3.0;
b is between 0 and 0.5;
c is between 3.5 and 5.5; and
d is a number sufficient to satisfy the valences of the other elements;

said catalyst being prepared by a coprecipitation method effected at a pH ranging from 2 to 5 and at a temperature between 20° and 90° C., by adding to a first solution containing cobalt in the form of the nitrate, a second solution containing molybdenum, vanadium, and optionally also tungsten, in the form of ammonium salts, thus obtaining a precipitate which is subjected to successive thermal treatments in air, comprising drying at 90°–130° C. for 10–20 hours, calcining at 200°–300° C. for 6–24 hours, and activation at 350°–450° C. for not less than two hours.

2. A process as defined in claim 1, characterized in that:

a is between 2.0 and 2.4;
b is between 0 and 0.3; and
c is between 3.9 and 4.3.

3. A process as defined in claim 1, characterized in that the catalyst is deposited on a carrier.

4. A process as defined in claim 1, characterized in that the reaction of the acrolein or methacrolein with the molecular oxygen is effected in the presence of gaseous diluents or of water vapor.

5. A process as defined in claim 1, characterized in that acrolein is oxidized to acrylic acid.

6. A process as defined in claim 1, characterized in that methacrolein is oxidized to methacrylic acid.

* * * * *